US008221796B2

(12) United States Patent
Gutierrez Martinez et al.

(10) Patent No.: US 8,221,796 B2
(45) **Date of Patent: *Jul. 17, 2012**

(54) COPPER-BASED FUNGICIDE/BACTERICIDE

(75) Inventors: Alfonso Gutierrez Martinez, Chihuahua (MX); Laura Elizabeth Bailon Cisneros, Chihuahua (MX); Pablo Diaz Toledo, Chihuahua (MX); Raul Salazar Franco, Mexico City (MX)

(73) Assignee: Albaugh, Inc., Ankeny, IA (US)

( * ) Notice: Subject to any disclaimer, the term of this patent is extended or adjusted under 35 U.S.C. 154(b) by 641 days.

This patent is subject to a terminal disclaimer.

(21) Appl. No.: 12/257,041

(22) Filed: Oct. 23, 2008

(65) Prior Publication Data

US 2009/0136581 A1 May 28, 2009

Related U.S. Application Data

(63) Continuation-in-part of application No. 11/410,147, filed on Apr. 25, 2006.

(51) Int. Cl.

| | |
|---|---|
| ***A61K 31/74*** | (2006.01) |
| ***A61K 31/765*** | (2006.01) |
| ***A61K 33/34*** | (2006.01) |
| ***A61K 59/20*** | (2006.01) |
| ***A01N 25/08*** | (2006.01) |

(52) U.S. Cl. .................. 424/630; 424/78.08; 424/78.33; 424/78.1; 424/409; 424/633; 514/772.6

(58) Field of Classification Search ............... 424/78.08, 424/78.33, 78.1, 409, 633, 630; 514/772.6
See application file for complete search history.

(56) References Cited

U.S. PATENT DOCUMENTS

| | | | |
|---|---|---|---|
| 4,020,180 | A | 4/1977 | Woerner |
| 4,075,326 | A | 2/1978 | Kuyama et al. |
| 4,181,786 | A | 1/1980 | Mune et al. |
| 4,409,358 | A | 10/1983 | Kraft et al. |
| 4,418,056 | A | 11/1983 | Gonzalez |
| 4,528,185 | A | 7/1985 | Kraft et al. |
| 4,770,694 | A | 9/1988 | Iwasaki et al. |
| 4,936,901 | A | 6/1990 | Surgant, Sr. et al. |
| 5,298,253 | A | 3/1994 | LeFiles et al. |
| 5,462,738 | A | 10/1995 | LeFiles et al. |
| 6,139,879 | A | 10/2000 | Taylor |
| 6,149,821 | A | 11/2000 | Rounds et al. |
| 6,436,421 | B1 | 8/2002 | Schindler |
| 6,471,976 | B1 | 10/2002 | Taylor et al. |
| 6,472,347 | B1 | 10/2002 | Naguib |
| 6,562,757 | B1 | 5/2003 | Ferrier et al. |
| 6,689,392 | B2 | 2/2004 | Lifshitz |
| 6,767,865 | B2 | 7/2004 | Den Tandt et al. |
| 6,849,276 | B1 | 2/2005 | Dufau et al. |
| 7,186,887 | B2 | 3/2007 | Kreps et al. |
| 7,238,654 | B2 | 7/2007 | Hodge et al. |
| 7,455,849 | B2 | 11/2008 | Utschig et al. |
| 2002/0136781 | A1 | 9/2002 | Huato et al. |
| 2006/0057217 | A1 | 3/2006 | Utschig et al. |
| 2007/0248673 | A1 | 10/2007 | Martinez et al. |

FOREIGN PATENT DOCUMENTS

| | | |
|---|---|---|
| WO | 9113552 | 9/1991 |
| WO | 2007123531 | 11/2007 |

*Primary Examiner* — Johann Richter
*Assistant Examiner* — Luke Karpinski
(74) *Attorney, Agent, or Firm* — Duane Morris LLP

(57) ABSTRACT

The present invention discloses an improved copper-based fungicide/bactericide composition. The improved composition offers higher biological activity over typical copper-based products, while requiring significantly less copper in the composition. The present invention also discloses methods of making the improved copper-based fungicide/bactericide composition. The present invention further discloses methods of using the improved copper-based fungicide/bactericide composition.

14 Claims, No Drawings

COPPER-BASED FUNGICIDE/BACTERICIDE

CROSS-REFERENCE TO RELATED APPLICATION

The present application is a continuation-in-part of application Ser. No. 11/410,147, filed Apr. 25, 2006.

FIELD OF THE INVENTION

The present invention relates generally to a bactericidal/fungicidal composition. More specifically, the present invention relates to a bactericidal/fungicidal composition that is based upon a non-leachable copper-citrate complex that is stabilized by a double dispersing system and that reduces the dose of copper used per hectare.

BACKGROUND OF THE INVENTION

Fungi are a large group of nongreen plants dependent upon the organic food made by photosynthesizing green plants. They represent a constant and ever present threat to many agricultural crops ranging from tropical and semi-tropical vegetation to temperate climate crops. Thus the control of phytopathogenic fungi is of great economic importance since fungal growth on plants or on parts of plants inhibits production of foliage, fruit or seed, and the overall quality of a cultivated crop. In addition, certain groups of fungi produce mycotoxins in infected crops, directly posing a health hazard to humans and animals. Fungicides are known in the art as either chemical or biological agents used to mitigate, inhibit or destroy fungi. To be economical, the cost of controlling plant diseases must be offset by increased crop yield and quality.

The use of $Cu^{2+}$ ions for protecting crops against phytopathogenic fungi has been known for a long time. As early as 1882, a Bordeaux mixture was used to control the downy mildew on grapes. The Bordeaux mixture consisted of a light blue gelatinous precipitate suspended in water and formed by reacting 4 pounds of copper sulfate with 4 pounds of hydrated lime (calcium hydroxide) in 50 gallons of water. Variations of the Bordeaux mixture have been made by changing the ratio of the components.

Presently, copper based fungicides/bactericides are used extensively in agriculture. It has been observed that various types of copper compounds can be used to effectively treat various plant pathogens, and are available in different types of formulations including wettable powders, emulsifiable concentrates, water-based flowables and dry flowables (also known as water dispersible granules). Dry flowable products are generally dustless, free-flowing, granular products. They are popular among users because the products can be formulated with a higher percentage of active ingredient, are easy to use and have improved shelf life compared to the aqueous fungicides/bactericides. Dry bactericides/fungicides can be stored for a long period of time, over wide extremes of temperature, without destroying the stability of the formulation. Dry bactericides/fungicides formulations also result in lower shipping cost.

While copper compounds have been known for their ability to control fungi/bacteria, the copper materials applied must be relatively non-toxic to the plants. Generally, inorganic copper compounds have been used because they have been observed to be non-phytotoxic, while most of the organic copper compounds have been found phytotoxic, especially in foliar applications.

With respect to the inorganic copper compounds, water soluble copper compounds are known to be extremely phytotoxic. As a result, water insoluble copper compounds are used as fungicides/bactericides. However, the low water solubility of the copper compounds presents a different kind of problem.

Biological activity of the copper-based fungicides/bactericides is measured by the free $Cu^{2+}$ ions available for consumption by the fungi or bacteria. The biological activity of a fungicide/bactericide increases with an increase in the amount of free $Cu^{2+}$ ions released. Therefore, the fungicides/bactericides formulated based on water insoluble copper compounds are normally applied in relatively large amounts to effectively control the phytopathogenic fungi. As a result, the relatively high level of copper detracts from cost effectiveness, contributes to soil residue contamination and raises the potential for phytotoxicity.

As an alternative to high level copper compound usage, the water insoluble copper compounds can be milled to fine particle size to increase the surface area of the compounds. The finer the copper compound, the more surface area it can cover with relatively small amounts of copper compounds. However, the methods employed to reduce the particle size of the copper compounds are not always cost effective. In addition, as a practical matter, it is difficult to disperse the finely milled copper compounds because of the tendency of fine particles to agglomerate.

Aside from process and formulation modifications, it is known that a copper complex or copper chelate can be used as a source of free $Cu^{2+}$ instead of water insoluble copper compounds. It has been demonstrated that certain types of copper complexes or chelates are substantially nonphytotoxic and effective fungicides/bactericides for agriculture use.

U.S. Pat. Nos. 5,462,738 and 5,298,253 describe a granular dry flowable bactericide/fungicide containing about 40%-80% of copper hydroxide.

U.S. Pat. No. 6,139,879 describes an aqueous bactericide/fungicide containing a complex of copper and ethylenediamine-N,N'-bis(2-hydroxyphenylacetic acid) (EDDHA).

U.S. Pat. No. 6,471,976 describes an aqueous bactericide/fungicide containing a complex of copper and a partially neutralized polycarboxylic acid. While the bactericides/fungicides reduce the usage of copper compounds, the bioavailable copper from the complexes based on copper hydroxide ranges only from 217 ppm to 3530 ppm.

U.S. Pat. No. 6,562,757 describes a plant-protection composition comprising a copper source in non-chelated form and a sparingly soluble calcium, zinc or manganese chelate. Upon application of the composition, copper chelates are formed in situ and gradually released to extend the application interval. U.S. Pat. No. 6,562,757 also describes a process of making the claimed composition by mixing and milling all the dry and powdery ingredients. While the gradual release of $Cu^{2+}$ ions may be advantageous, it is desirable for a fungicide/bactericide to have an effective initial $Cu^{2+}$ ion concentration to provide immediate antifungal/antibacterial effect. It is also desirable to have a process of making a fungicide/bactericide substantially dust-free. Additionally, the use of chelating agents and dispersants in large amounts substantially increases the cost and renders the formulation economically infeasible.

Global health and environmental regulations are becoming more and more stringent with respect to unmanaged or unnecessary fungicide/bactericide residues. Farmers around the world are facing a paradox. On one hand, the need to control destructive pathogens requires more fungicide/bactericide use. On the other hand, increasing pressures from regulatory agencies demand less chemical residue on crops and in the soil.

Therefore, a need exists for a copper-based fungicide/bactericide having high biological activity compared with existing copper-based products, while requiring significantly less copper in the formulation. A need exists for a copper-based fungicide/bactericide having both an immediate and extended antifungal/antibacterial effect. A need also exists for a process to make and use such fungicide/bactericides in a cost effective and environmentally friendly manner. A way to meet these needs has now been found using the present invention.

SUMMARY OF THE INVENTION

The present invention is directed to an improved copper-based fungicide/bactericide composition. The improved composition offers higher biological activity and greater cost-effectiveness compared with existing copper-based products, while requiring significantly less copper in the composition.

The improved copper-based fungicide/bactericide composition of present invention comprises:

a. between about 5.0% to about 39.0% by weight (based on the total weight of all dry ingredients) of copper hydroxide;

b. between about 0.2% and about 10.0% by weight of a water soluble copper chelator, which is a carboxylic acid derivative;

c. between about 2.0% and about 15.0% by weight of a first dispersant, wherein said first dispersant is a block copolymer non-ionic surfactant having an average molecular weight of between about 1,000 and 15,000 or a polycarboxylic acid derivative having a pH of between about 5 and about 10 and an average molecular weight of between about 1,000 and about 37,000, or combinations thereof;

d. up to about 10.0% by weight of a second dispersant, which is lignin sulfonate, naphthalenesulfonate or combinations thereof;

e. between about 0.5% and about 60.0% by weight of a filler; and f. optionally between about 0.01% and about 1.50% by weight of an antifoaming agent, and/or a stabilizer, and/or a wetting agent, and/or combinations thereof.

The present invention is also directed to a method of making the improved copper-based fungicide/bactericide composition. The method comprises:

a. combining between about 5.0% to about 39.0% by weight (based on the total weight of all dry ingredients) of a copper hydroxide wet cake having about 40 to about 60% solid content with, i. between about 0.2% and about 10.0% by weight of a water soluble copper chelator which is a carboxylic acid derivative, ii. between about 2.0% and about 15.0% by weight of a first dispersant, which is a block copolymer non-ionic surfactant having an average molecular weight of between about 1,000 and about 15,000, or a polycarboxylic acid derivative having a pH of between about 5 and about 10 and an average molecular weight of between about 1,000 and about 37,000, or combinations thereof, iii. up to about 10.0% by weight of a second dispersant, which is a lignin sulfonate, naphthalenesulfonate, or combinations thereof, iv. between about 0.5% and about 60.0% by weight of a filler, and v. optionally an antifoaming agent, and/or a stabilizer, and/or a wetting agent, and/or a combination thereof, b. mixing to obtain a homogenous slurry; and c. drying said slurry to a moisture content of less than about 4.0%.

The present invention is further directed to a method of using the improved copper-based fungicide/bactericide composition. The method comprises applying to the plants an effective amount of fungicide/bactericide composition of the invention.

DETAILED DESCRIPTION OF THE INVENTION

The improved composition of the present invention releases and disperses free $Cu^{2+}$ ions up to 10 times more than that of typical copper-based formulations. For example, the present invention releases about 25,000 ppm (parts per million) of $Cu^{2+}$ ions from a copper hydroxide based fungicide/bactericide, compared to about 2,500 ppm of $Cu^{2+}$ ions from typical copper hydroxide based fungicides/bactericides.

A fungicide/bactericide formulation may be produced in accordance with the present invention by mixing between 5.0% to 39.0% by weight (based on the total weight of all dry ingredients) of a copper hydroxide wet cake with, i. between 0.2% and 10.0% by weight of a water soluble copper chelator which is a carboxylic acid derivative, ii. between about 2.0% and about 15.0% by weight of a first dispersant, which is a block copolymer non-ionic surfactant having an average molecular weight of between about 1,000 and about 15,000, or a polycarboxylic acid derivative having a pH of between about 5 and about 10 and an average molecular weight of between about 1,000 and about 37,000, or combinations thereof, iii. up to about 10.0% by weight of a second dispersant, which is lignin sulfonate, naphthalenesulfonate or combinations thereof, iv. between 0.5% and 60.0% by weight of a filler, and v. optionally, an antifoaming agent, and/or stabilizer, and/or wetting agent and/or the combinations thereof to form a homogeneous aqueous slurry.

The slurry is then spray dried in conventional spray drying equipment to obtain dry flowable granules with an average particle size of less than about 8 microns.

The copper hydroxide wet cake may be produced by mixing copper oxychloride with caustic soda to form copper hydroxide and passing the reaction mixture through a rotary filter to dewater and obtain the copper hydroxide wet cake having about 40-60% solid content, more preferably having about 45-55% solid content, most preferably having about 50% solid content.

The concentration of copper hydroxide (based on the total weight of all the dry ingredients) used in the present invention is in the range of about 5% to about 39% by weight, preferably about 10% to about 39%, more preferably about 10% to about 30%, most preferably about 10% to about 25%.

The carboxylic acid derivatives useful as copper chelators in the present invention include water soluble organic compounds containing two or more carboxylate functionalities, and their salts. The preferred carboxylic acid derivatives are citric acid, tartaric acid, oxalic acid, malic acid, fumaric acid, succinic acid, glutaric acid, adipic acid, their metal and ammonium salts. The most preferred carboxylic acid derivatives are citric acid and sodium citrate.

The concentration of carboxylic acid derivatives (based on the total weight of all the dry ingredients) used in the present invention is in the range of about 0.2% to about 10%, preferably about 1% to about 6%, more preferably about 4% to about 6%.

The block copolymer non-ionic surfactants useful in the present invention include non-ionic surfactants used in emulsifiable and suspension concentrates. Suitable block copolymers are polyalkylene oxide block copolymers having a molecular weight of between about 1,000 to about 15,000. The preferred block copolymer non-ionic surfactant is Toximul® 8323 available from Stephan Company, Illinois, U.S.A.

The polycarboxylic acid derivatives useful in the present invention include polyacrylic acid derivatives. The polyacrylic acid derivatives can be prepared by neutralizing polyacrylic acids having a molecular weight of between about 1,000 and 37,000, preferably between about 5,000 and about 37,000. The polyacrylic acid is neutralized to a pH of between about 5 and about 10 by adding to the polyacrylic acid a neutralizing agent. Suitable neutralizing agents include sodium hydroxide, potassium hydroxide, $NaHCO_3$, $Na_2CO_3$ and the like. The preferred polyacrylic acid derivative is Orotan® 850, available from Rohm and Haas Company, Pennsylvania, U.S.A. Orotan® 850 is a sodium salt of polyacrylic acid.

Other polycarboxylic acid derivatives can also be used in the present invention. Suitable polycarboxylic acids useful in the present invention include polymethacrylic acids; copolymers of acrylic acid and acrylamide, methacrylamide, acrylate esters (e.g., methyl, ethyl and butyl), methacrylic acid, methacrylate esters (e.g., methyl and ethyl) and maleic anhydride; carboxymethylcellulose; and maleic acid polymers and copolymers with butadiene and maleic anhydride.

The foregoing block copolymer non-ionic surfactants and polycarboxylic acid derivatives may be used alone or in combination to achieve the optimal results.

When used in combination, a suitable ratio of the block copolymer non-ionic surfactant to the polycarboxylic acid derivatives may be between 10:1 to 1:10, preferably between 5:1 to 1:5, more preferably between 2:1 to 1:2.

Fillers for granules, wettable powders and dry flowables of copper-based fungicide/bactericide are known in the art. Suitable fillers include diatomaceous earth, calcium carbonate, calcium bentonite clay and sodium bentonite clay. The preferred diatomaceous earth is available under the trade name Celite 350, having a particle size distribution of $d_{10}$=3.0-3.5 microns, $d_{50}$=10-13 microns and $d_{90}$=20-25 microns. It is available from Celite World Minerals Inc. in California, U.S.A. The preferred calcium carbonate has a particle size distribution of $d_{10}$=0.5-0.6 microns, $d_{50}$=1.5-1.7 microns and $d_{90}$=8-10 microns. It is available from Qualymin of Monterrey, Mexico.

Lignin sulfonates and naphthalenesulfonates useful as dispersants are known in the art. The preferred lignin sulfonate is available under the trade name Wanin® DP 734 FI, a sodium salt of lignin polymer. It is available from Borregaard Lignotech, Finland. The preferred naphthalenesulfonate is available under the trade name Morwet® D-425, a sodium salt of naphthalene sulfonate condensate. It is available from Akzo Nobel Surface Chemistry LLC, Texas, U.S.A. Lignin sulfonates and naphthalenesulfonates may be used alone or in combination to achieve the optimal results.

The copper based fungicide/bactericide compositions can optionally include other formulation additives, such as wetting agents, antifoam agents and stabilizers. The wetting agents, antifoaming agents and stabilizers are known in the art. The preferred wetting agent is Genapol® X060, a fatty alcohol polyglycol ether non-ionic surfactant, available from Clariant Corporation of Charlotte, N.C., U.S.A. The preferred antifoam agent is AF® 365 Antifoam, a polydimethylsiloxane antifoam emulsion, available from General Electric of Greenwich, Conn., U.S.A. The preferred stabilizer is glycerol. The wetting agents, antifoam agents and stabilizers can each be incorporated into the compositions in amounts between about 0.01% and about 1.50% by weight (based on the total weight of all dry ingredients). They may be used alone or in combination to achieve the optimal results.

The slurry can be air dried, oven dried or spray dried. Preferably, the slurry is spray dried to form a dry flowable granular product by using a spray dryer equipped with an atomizer. The spray drying chamber has an inlet temperature of about 300° C., and an outlet temperature of about 90° C. The resulting granular product has moisture content of less than about 4.0%, preferably less than about 2.0%. The resulting granular product has an average particle size of less than about 8 microns, preferably less than about 6 microns, more preferably less than about 4 microns.

Using techniques known in the art, the fungicide/bactericide compositions of the present invention can be prepared in other forms, such as flakes, powders, tablets, pellets and solutions.

The fungicide/bactericide compositions are tested for biocopper. The term "biocopper" means free $Cu^{2+}$ ions available for consumption by the fungi or bacteria. The "biocopper" value can be measured by Atomic Absorption Spectrophotometric methods as exemplified below:

a. Preparation of Standard Copper Solutions

Standard solutions of 5, 10, 15, 20, 30 and 35 ppm are prepared by dilution from commercially available copper standard solution of 1000 ppm. A working solution is prepared from the standard stock solution by taking 10.0 mL of standard solution (1000 ppm), transferring it to 100 mL volumetric flask and diluting it to 100 mL with de-ionized water to obtain a standard solution containing 100 μg/mL of copper. Standard solutions are prepared by taking 5, 10, 15, 20, 30 and 35 mL portions of this solution and transferring it to 100 mL volumetric flasks; in each case diluting to 100 mL with de-ionized water to obtain standard solutions containing 5, 10, 15, 20, 30 and 35 μg/mL of copper.

b. Preparation of the Calibration Curve

The absorbance of the standard solutions is measured by atomic absorption spectrophotometry in an air-acetylene flame at 324.7 nm. The burner must be in perpendicular position with respect to the light beam. A calibration curve of absorption against amount of copper is plotted.

c. Determination of Biocopper

The fungicide/bactericide of the present invention (about 0.1 g) of the composition is weighed (to the nearest 0.0001 g) and transferred to a 250 mL conical flask, 100 mL of de-ionized water is added and stirred for 15 minutes at 20-25° C. About 40 mL of the supernatant is filtered through a 45 microns Millipore filter and read in the Atomic Absorption equipment using the burner positioned perpendicular to the light beam.

Calculation $$\text{Biocopper(ppm)}=[C*100)]/W$$

Where C is the concentration (μg/mL) read from the equipment and W is the sample weight in grams. The factor 100 refers to the volume of water employed for the analysis.

The fungicide/bactericide compositions of the present invention may be applied directly to the leaves of a plant at a rate of preferably between about 0.5 and about 12.0 pounds per acre depending on the specific plants to be protected or treated. The fungicide/bactericide compositions of the present invention may also be mixed with water and then sprayed onto the plants using conventional agricultural sprayers and spraying techniques known in the art. The mixing ratio of granulates and water is between about 2:10,000 (w/w) and 5:1,000, more preferably between about 3:10,000 and about 2:1,000, and most preferably 5:10,000. The rate of spray application is preferably between about 10 and 165 gallons per acre depending on the specific plants to be protected or treated.

The fungicide/bactericide compositions of the present invention are useful for treating bacterial and fungal diseases on various plants including citrus, such as grapefruit, lemon, lime, orange, tangelo and tangerine; field crops, such as alfalfa, oats, peanuts, potatoes, sugar beets, wheat, and barley; small fruits, such as blackberry, blueberry, cranberry, currant, gooseberry, raspberry and strawberry; tree crops, such as almond, apple, apricot, avocado, banana, cacao, cherry, coffee, filberts, litchi, mango, nectarine, olive, peach, pear, pecan, plum, pistachio, prune, sugar apple and walnut; vegetables, such as bean, broccoli, Brussels sprout, cabbage, cantaloupe, carrot, cauliflower, celery, collards, cucumber, eggplant, honeydew, lettuce, muskmelon, onion, pea, pepper, pumpkin, squash, spinach, tomato, watercress and watermelon; vines, such as grape, hops and kiwi; miscellaneous, such as ginseng, live oak and sycamore and ornamentals, such as *aralia*, azalea, begonia, bulbs (Easter lily, tulip, gladiolus), carnation, chrysanthemum, *cotoneaster*, Douglass fir, euonymus, India hawthorn, ivy, pachysandra, periwinkle, philodendron, pyracantha, quince, rose, turfgrass and yucca (Adams-Needle).

The fungicide/bactericide composition of the present invention is useful for treating plants with fungal or bacterial diseases, such as melanose, scab, pink pitting, greasy spot, brown rot, *phytophthora*, citrus canker, *xanthomonas* and cerospora leaf spots, black leaf spot (*alternaria*), *alternaria* blight, blossom blight, *botrytis* blight, powdery mildew, *xanthomonas* leaf spot, leaf and cane spot, anthracnose, pseudomonas leaf spot, *septoria* leaf spot, entomosporium leaf spot, volutella leaf blight, *phomopsis* stem blight, bacterial leaf spot, fire blight, black spot, leaf curl, coryneum blight (shot hole), blossom blight, pseudomonas blight (blossom blast), shuck and kernel rot (*Phytophthora cactorum*), zonate leafspot (*Cristulariella pyramidalis*), walnut blight, bacterial blight (halo and common), brown spot, black rot (xanthomonas), downy mildew, *cercospora* early blight, *septoria* late blight, angular leaf spot, *phomopsis*, purple blotch, bacterial speck, gray leaf mold, *septoria* leaf spot, dead bud (*Pseudomonas syringae*), *Erwinia herbicola, Pseudomonas fluorescens*, stem blight, ball moss, *leptosphaerulina* leaf spots, *helminthosporium* spot blotch, *cercospora* leaf spot, leaf spot, iron spot, cane spot, fruit rot, blossom brown rot, bacterial blast (pseudomonas), European canker, crown or collar rot, sigatoka, black pitting, black pod, coffee berry disease (*Collectotrichum coffeanum*), leaf rust (*Hemileia vastatrix*), iron spot (*Cercospora coffeicola*), pink disease (*Corticium salmonicolor*) eastern filbert blight, and peacock spot.

The following examples are illustrative of the present invention and are not intended to limit the scope of the invention as set forth in the appended claims.

EXAMPLE 1

Pump a calculated amount of copper hydroxide wet cake (30% solid content) into a formulation tank and add other ingredients in Table 1 below. Mix all the ingredients to form a substantially homogeneous slurry. Allow a five-minute waiting period between each addition to ensure good dissolution and dispersion of added ingredients. The resulting slurry is then pumped to a spray dryer feed tank to be spray dried to dry flowable granular products. The spray dryer is equipped with an atomizer, and has an inlet chamber temperature of about 300° C. and an outlet temperature of about 90° C. The dry granular products are collected and packaged, having moisture content of less than about 2.0%.

TABLE 1

| Copper Hydroxide 25% | |
|---|---|
| Ingredients | Pounds* |
| Copper hydroxide wet cake (30% solid content) | 2120.6 |
| Citric Acid | 248 |
| Toximul 8323 | 220.4 |
| Orotan 850 | 330.6 |
| Diatomaceous earth | 2422.4 |
| GenapolX060 | 55.11 |
| AF 365 Antifoam | 5.51 |
| Glycerol | 55.11 |

*Weight is based on the total weight of all dry ingredients.

EXAMPLE 2

The granules are made as in Example 1 and are measured for biocopper:

TABLE 2

| Ingredients | FORMULATION | | | |
|---|---|---|---|---|
| Wt %* | A (Wt %*) | B (Wt %*) | C (Wt %*) | D (Wt %*) |
| Copper hydroxide | 23.04 | 23.04 | 38.46 | 38.46 |
| Citric Acid | — | 4.50 | — | 4.50 |
| Toximul 8323 | 4.00 | 4.00 | 4.00 | 4.00 |
| Orotan 850 | — | 6.00 | — | 6.00 |
| Diatomaceous earth | 10.00 | 10.00 | 50.34 | 8.00 |
| Calcium carbonate | 55.88 | 50.38 | — | 36.84 |
| Naphthalen-sulfonate | 5.00 | — | 5.00 | — |
| Genapol X060 | 1.00 | 1.00 | 1.00 | 1.00 |
| AF 365 Antifoam | 0.08 | 0.08 | 0.20 | 0.20 |
| Glycerol | 1.00 | 1.00 | 1.00 | 1.00 |
| Biocopper | 6,000 ppm | 30,600 ppm | 5,500 ppm | 30,000 ppm |

*Wt % is based on the total weight of all dry ingredients.

As can be seen from Table 2, the fungicide/bactericide compositions containing water soluble carboxylic acid derivatives, such as citric acid have a significantly higher biocopper content (comparing formulation A to B, or comparing formulation C to D).

EXAMPLE 3

The granules A1, B1, C1, D1, E1, F1, G1, H1, I1 and J1 are made as in Example 1 and are measured for biocopper:

TABLE 3

| Ingredients | Formulations | | | | | | | | | |
|---|---|---|---|---|---|---|---|---|---|---|
| | A1 | B1 | C1 | D1 | E1 | F1 | G1 | H1 | I1 | J1 |
| Copper Hydroxide | 33.84% | 33.84% | 33.84% | 33.84% | 33.84% | 33.84% | 33.84% | 33.84% | 33.84% | 33.84% |
| Carboxylic acid derivatives | 6.00% | 2.50% | 2.50% | 2.50% | 2.50% | 2.50% | 4.50% | 4.50% | 5.00% | 5.00% |
| Glycerol | 1.00% | 1.00% | 1.00% | 1.00% | 1.00% | 1.00% | 1.00% | 1.00% | 1.00% | 1.00% |
| Wetting agent | 0.25% | 0.25% | 0.25% | 0.25% | 0.25% | 0.25% | 1.00% | 1.00% | 0.25% | 0.25% |
| Antifoaming agent | 0.02% | 0.02% | 0.02% | 0.02% | 0.02% | 0.02% | 0.50% | 0.50% | 0.50% | 0.50% |
| Diatomaceous earth | 49.89% | 56.39% | 60.39% | 57.39% | 57.39% | 57.39% | 0.80% | 4.50% | 4.50% | 4.50% |
| Block copolymer non-ionic surfactant | 3.00% | — | — | — | — | — | 4.00% | 4.00% | 2.50% | 3.00% |
| Naphthalenesulfonate | 6.00% | — | — | — | — | — | — | — | 5.00% | 5.00% |
| Calcium carbonate | — | — | — | — | — | — | 48.36% | 40.04% | 44.41% | 43.91% |
| Polyacrylic acid derivatives (molecular weight 1,000 Mw) | — | — | — | — | 5.00% | — | — | — | — | — |
| Polyacrylic acid derivatives (molecular weight 5,000 Mw) | — | — | — | 5.00% | — | — | — | — | — | — |
| Polyacrylic acid derivatives (molecular weight 5,000 Mw) | — | — | — | — | — | — | — | — | — | — |
| Polyacrylic acid derivatives (molecular weight 1,0000 Mw) | — | — | 2.00% | — | — | — | — | — | — | — |
| Polyacrylic acid derivates (molecular weight 11,000 Mw) | — | 6.00% | — | — | — | — | — | — | — | — |
| Polyacrylic acid derivates (molecular weight 30,000 Mw) | — | — | — | — | — | — | 6.00% | 6.00% | — | — |
| Polyacrylic acid derivates (molecular weight 18,000 Mw) | — | — | — | — | — | 5.00% | — | — | — | — |
| Calcium bentonite clay | — | — | | — | — | — | — | — | — | — |
| Sodium bentonite clay | — | — | | — | — | — | — | — | — | — |
| Lignosulfonates | — | — | | — | — | — | — | — | 3.00% | 3.00% |
| Biocopper (ppm) | 29,200 | 11,800 | 11,200 | 11,500 | 10,000 | 11,500 | 25,900 | 25,000 | 28,000 | 27,900 |

EXAMPLE 4

The granules K1, L1, M1, N1, Ň1, O, P, Q, R and S are made as in Example 1 and are measured for biocopper:

TABLE 4

| Ingredients | Formulations | | | | | | | | | |
|---|---|---|---|---|---|---|---|---|---|---|
| | K1 | L1 | M1 | N1 | Ň1 | O | P | Q | R | S |
| Copper Hydroxide | 33.84% | 33.84% | 38.46% | 38.46% | 38.46% | 38.46% | 38.46% | 38.46% | 33.84% | 38.46% |
| Carboxylic acid derivates | 5.00% | 5.00% | 4.50% | 4.50% | 6.00% | 6.00% | 6.00% | 6.00% | 4.50% | 4.50% |
| Glycerol | 1.00% | 1.00% | 1.00% | 1.00% | 1.00% | 1.00% | 1.00% | 1.00% | 1.00% | 1.00% |
| Wetting agent | 0.25% | 0.25% | 0.25% | 0.25% | 0.25% | 0.25% | 0.25% | 0.25% | 0.25% | 0.25% |
| Antifoaming agent | 0.50% | 0.50% | 0.50% | 0.50% | 0.50% | 0.50% | 0.50% | 0.50% | 0.50% | 0.50% |
| Diatomaceous earth | 4.50% | 48.41% | 4.50% | 4.50% | 48.79% | 48.79% | — | — | — | — |
| Block copolymer non-ionic surfactant | 3.00% | 3.00% | 4.00% | 4.00% | 2.00% | 2.00% | 4.00% | 4.00% | 4.00% | 4.00% |
| Naphthalenesulfonate | 5.00% | 5.00% | 5.00% | 5.00% | — | — | — | — | — | — |
| Calcium carbonate | 42.91% | — | 41.79% | 38.79% | — | — | 46.79% | 46.79% | — | — |
| Polyacrylic acid derivates (molecular weight 5,000 Mw) | — | — | — | — | 3.00% | — | 3.00% | — | — | — |
| Polyacrylic acid derivates (molecular weight 5,500 Mw) | — | — | — | — | — | 3.00% | — | 3.00% | — | — |
| Polyacrylic acid derivates (molecular weight 3,0000 Mw) | — | — | — | — | — | — | — | — | 6.00% | 6.00% |
| Calcium bentonite clay | — | — | — | — | — | — | — | — | 40.92% | 36.88% |
| Sodium bentonite clay | — | — | — | — | — | — | — | — | 8.99% | 8.41% |
| Lignosulfonates | 4.00% | 3.00% | — | 3.00% | — | — | — | — | — | — |
| Biocopper (ppm) | 27,000 | 26,900 | 24,500 | 23,000 | 29,000 | 30,000 | 28,700 | 27,200 | 26,000 | 27,500 |

EXAMPLE 5

The granules are made as in Example 1 and measured for biocopper.

TABLE 5

| | Formulations | | | |
|---|---|---|---|---|
| Ingredients | Metallic Cu 10% | Metallic Cu 15% | Metallic Cu 20% | Metallic Cu 25% |
| Copper Hydroxide | 15.36% | 23.04% | 30.72% | 38.40% |
| Citric Acid | 4.50% | 4.50% | 6.00% | 6.00% |
| Glycerol | 1.00% | 1.00% | 1.00% | 1.00% |
| Fatty alcohol polyglycol ether | 1.00% | 1.00% | 1.00% | 0.25% |
| Polydimethylsiloxane | 0.10% | 0.10% | 0.10% | 0.50% |
| Diatomaceous earth | 10.00% | 10.00% | 8.00% | 8.00% |
| Toximul 8323/33 | 4.00% | 4.00% | 4.00% | 4.00% |
| Calcium carbonate | 58.04% | 50.36% | 43.18% | 35.85% |
| Polyacrylate acid derivates (molecular weight 30 000 Mw) | 6.00% | 6.00% | 6.00% | 6.00% |
| BIOCOPPER | 32,100 | 30,600 | 28,800 | 25,100 |

EXAMPLE 6

TABLE 6

| | Comparative Examples | | COH 20% HB Copper |
|---|---|---|---|
| Active ingredient | Copper Hydroxide* Wettable powder | Bordeaux Mixture* Wettable powder | hydroxide Dry flowable |
| Metallic Copper | 40% | 15.5% | 20% |
| Chelating agent | Insoluble citrates (Ca, Zn, Mn) 18.7% | Insoluble citrates (Ca, Zn, Mn) 6.8-28.8% | Citric acid 6% |
| Dispersant | 1.7% lignosulfonate + 4% naphthalenesulfonate | 1.7% lignosulfonate + 4% naphthalenesulfonate | PAA 6% + block copolymer 4%-6% |
| Filler | Kaolin | Kaolin | $CaCO_3$ + diatomaceous earth |
| Suspensibility | 78%* | 79%* | 84% |
| Soluble copper | 11,200 ppm* | 10,700 ppm (6.8%)* 24,500 ppm (28.8%)* | 30,000 ppm (6%) |

*The comparative examples are prepared according to U.S. Pat. No. 6,562,757

EXAMPLE 7

The granules T, U and V are made as in Example 1 and measured for initial suspensibility and extended stability at 7 days and 14 days. Initial suspensibility of each formulation is determined according to CIPAC method MT 184 and then a sample of every formulation is submitted to accelerated stability test at 54° C. according to CIPAC method MT 46.

TABLE 7

| | FORMULATIONS | | |
|---|---|---|---|
| Ingredients | T | U | V |
| Copper Hydroxide | 30.72 | 30.72 | 30.72 |
| Citric Acid | 4.5 | 4.5 | 4.5 |
| Glycerol | 1.0 | 1.0 | 1.0 |
| Fatty alcohol polyglycol ether | 1.0 | 1.0 | 1.0 |
| Polydimethylsiloxane | 0.1 | 0.1 | 0.1 |
| Diatomaceous earth | 11.47 | 11.47 | 11.47 |
| Calcium carbonate | 45.21 | 45.21 | 39.21 |
| Toximul 8323/33 | 0.0 | 6.0 | 6.0 |
| OROTAN 850 | 6.0 | 0.0 | 6.0 |
| Initial suspensibility | 89.27% | 53.41% | 90.8% |
| 7 days stability | 59.23% | 15.09% | 76.9% |
| 14 days stability | 55.67% | 11.76% | 70.98% |

As can be seen from Table 7, the formulation V containing both Toximul 8323/33 and OROTAN 850 exhibits increased stability compared to formulations T or U that contain either Toximul 8323/33 or OROTAN 850.

The fungicide/bactericides of the present invention, are tested on vine, tomato and apple plants using a variety of fungal targets.

| | Crop | | | | |
|---|---|---|---|---|---|
| | Vine *Vitis Vinifera* | Vine *Vitis Vinifera* | Tomato *Lycopersicon esculentum* | Apple *Malus sylvestris* | Apple *Pyrus communis* |
| Variety | Montepulciano | Chardonnay | Olinda | Red Chief | Santa María |
| Target | Downey Mildew | Downey mildew | Late blight | *Venturia inaequalis* | *Erwinia amylovora* |

The results of the tests are summarized in the following tables. In addition to % disease incidence, the results are also expressed in terms of grams of metallic copper used per hectare (Cu/ha) and relative metallic copper among several formulations and commercially available Kocide® 2000 and copper oxychloride (COC).

Metallic copper per hectare is calculated according to the following expression:

Cu/ha=(Dose*concentration)/100

Relative metallic copper is calculated by dividing metallic copper per hectare by 183.75. The value 183.75 is used as a reference value (Kocide® 2000 metallic copper/ha value) in order to compare the activity of the fungicide/bactericide of the present invention to commercially available Kocide® 2000 (183.75 g/ha).

EXAMPLE 8

TABLE 8

| Vine Montepulciano - Leaves damage | | | | | | |
|---|---|---|---|---|---|---|
| Product | Dose | Metallic copper per hectare (Cu/ha) | Relative metallic copper | % Disease incidence after 4 weeks | % Disease incidence after 7 weeks | % Efficacy Abbott's method |
| Untreated | — | — | — | 19 | 90 | — |
| COH 20% HB | 400 g/ha | 80 g/ha | 0.43 | 8 | 44 | 51 |
| COH 20% HB | 500 g/ha | 100 g/ha | 0.54 | 5 | 31 | 65 |
| COH 20% HB | 600 g/ha | 120 g/ha | 0.65 | 3 | 24 | 73 |
| Kocide ® 2000 (COH 35%) | 525 g/ha | 183.75 g/ha | 1.0 | 2 | 23 | 74 |
| Commercial COC 50% | 1500 g/ha | 750 g/ha | 4.08 | 2 | 13 | 85 |

COH: Copper Hydroxide

COC: Copper Oxychloride

EXAMPLE 9

TABLE 9

| Vine Montepulciano - Diseased bunch | | | | | | |
|---|---|---|---|---|---|---|
| Product | Dose | Metallic copper per hectare (Cu/ha) | Relative metallic copper | % Disease incidence after 4 weeks | % Disease incidence after 7 weeks | % Efficacy Abbott's method |
| Untreated | — | — | — | 5 | 25 | — |
| COH 20% HB | 400 g/ha | 80 g/ha | 0.43 | 2 | 11 | 56.6 |
| COH 20% HB | 500 g/ha | 100 g/ha | 0.54 | 1 | 5.3 | 78.8 |
| COH 20% HB | 600 g/ha | 120 g/ha | 0.65 | 1 | 3 | 87.9 |
| Kocide ® 2000 (COH 35%) | 525 g/ha | 183.75 g/ha | 1.0 | 1 | 3.3 | 86.9 |
| Commercial COC 50% | 1500 g/ha | 750 g/ha | 4.08 | 1 | 4.8 | 80.8 |

Phytotoxicity is not observed with the fungicide/bactericide of the present invention, COH 20% HB. At 600 g of copper hydroxide per hectare, COH 20% HB has an efficacy statistically comparable with that of Kocide® 2000.

EXAMPLE 10

TABLE 10

| Vine Chardonnay - Leaves damage | | | | | | |
|---|---|---|---|---|---|---|
| Product | Dose | Metallic copper per hectare (Cu/ha) | Relative metallic copper | % Disease incidence after 4 weeks | % Disease incidence after 8 weeks | % Efficacy Abbott's method |
| Untreated | — | — | — | 32.8 | 54.8 | — |
| COH 20% HB | 400 g/ha | 80 g/ha | 0.43 | 8 | 13.3 | 75.8 |
| COH 20% HB | 500 g/ha | 100 g/ha | 0.54 | 7.3 | 12 | 78.1 |
| COH 20% HB | 600 g/ha | 120 g/ha | 0.65 | 5.3 | 9 | 83.6 |
| Kocide ® 2000 (COH 35%) | 525 g/ha | 183.75 g/ha | 1.0 | 4.3 | 13.5 | 75.3 |
| Commercial COC 50% | 1500 g/ha | 750 g/ha | 4.08 | 3.8 | 6.3 | 88.6 |

EXAMPLE 11

TABLE 11

| Vine Chardonnay - Diseased bunch | | | | | | |
|---|---|---|---|---|---|---|
| Product | Dose | Metallic copper per hectare (Cu/ha) | Relative metallic copper | % Disease incidence after 4 weeks | % Disease incidence after 8 weeks | % Efficacy Abbott's method |
| Untreated | — | — | — | 0 | 1.5 | — |
| COH 20% HB | 400 g/ha | 80 g/ha | 0.43 | 0 | 0 | 100 |
| COH 20% HB | 500 g/ha | 100 g/ha | 0.54 | 0 | 0 | 100 |
| COH 20% HB | 600 g/ha | 120 g/ha | 0.65 | 0 | 0 | 100 |
| Kocide ® 2000 (COH 35%) | 525 g/ha | 183.75 g/ha | 1.0 | 0 | 0 | 100 |
| Commercial COC 50% | 1500 g/ha | 750 g/ha | 4.08 | 0 | 0 | 100 |

Phytotoxicity is not observed with the fungicide/bactericide of the present invention, COH 20% HB. At 500 g of copper hydroxide per hectare, COH 20% HB has an efficacy statistically comparable with that of Kocide® 2000.

EXAMPLE 12

TABLE 12

| Tomatoes - Leaves damage | | | | | | |
|---|---|---|---|---|---|---|
| Product | Dose | Metallic copper per hectare (Cu/ha) | Relative metallic copper | % Disease incidence after 4 weeks | % Disease incidence after 8 weeks | % Efficacy Abbott's method |
| Untreated | — | — | — | 0 | 91.9 | — |
| COH 20% HB | 400 g/ha | 80 g/ha | 0.43 | 0 | 6.9 | 92.5 |
| COH 20% HB | 500 g/ha | 100 g/ha | 0.54 | 0 | 0.9 | 99 |
| COH 20% HB | 600 g/ha | 120 g/ha | 0.65 | 0 | 0.9 | 99 |
| Kocide ® 2000 (COH 35%) | 525 g/ha | 183.75 g/ha | 1.0 | 0 | 0.3 | 99.7 |
| Commercial COC 50% | 1500 g/ha | 750 g/ha | 4.08 | 0 | 0.9 | 99 |

Phytotoxicity is not observed with the fungicide/bactericide of the present invention, COH 20% HB. At 500 g of copper hydroxide per hectare, COH 20% HB has an efficacy statistically comparable with that of Kocide® 2000.

EXAMPLE 13

TABLE 13

| Apples - Leaves damage | | | | | | |
|---|---|---|---|---|---|---|
| Product | Dose | Metallic copper per hectare (Cu/ha) | Relative metallic copper | % Disease incidence after 4 weeks | % Disease incidence after 7 weeks | % Efficacy Abbott's method |
| Untreated | — | — | — | 0 | 18.3 | — |
| COH 20% HB | 400 g/ha | 80 g/ha | 0.43 | 0 | 0 | 100 |
| COH 20% HB | 500 g/ha | 100 g/ha | 0.54 | 0 | 0 | 100 |
| COH 20% HB | 600 g/ha | 120 g/ha | 0.65 | 0 | 0 | 100 |
| Kocide ® 2000 (COH 35%) | 525 g/ha | 183.75 g/ha | 1.0 | 0 | 0 | 100 |
| Commercial COC 50% | 1500 g/ha | 750 g/ha | 4.08 | 0 | 0 | 100 |

Phytotoxicity is not observed with the fungicide/bactericide of the present invention, COH 20% HB. At 400 g of copper hydroxide per hectare, COH 20% HB has an efficacy statistically comparable with that of Kocide® 2000.

EXAMPLE 14

TABLE 14

| Vine Chardonnay - Leaves damage | | | | |
|---|---|---|---|---|
| Product | Dose | Metallic copper per hectare (Cu/ha) | Relative metallic copper/ha | % Efficacy Abbott's method |
| COH 20% HB | 400 g/ha | 80 g/ha | 0.43 | 75.8 |
| COH 20% HB | 500 g/ha | 100 g/ha | 0.54 | 78.1 |
| COH 20% HB | 600 g/ha | 120 g/ha | 0.65 | 83.6 |
| Kocide ® 2000 (COH 35%) | 525 g/ha | 183.75 g/ha | 1.0 | 75.3 |
| Commercial COC 50% | 1500 g/ha | 750 g/ha | 4.08 | 88.6 |

According to results presented in Tables 8-14, the fungicide/bactericide of the present invention exhibits comparable or higher efficacy on various plant species, while applied at a much lower amount of metallic copper per hectare as compared to reference commercial products. For example, in Table 8, COH 20% HB of the present invention, exhibits efficacy and % disease incidence similar to Kocide® 2000, while using only 65% (120 g/ha vs. 183.75 g/ha metallic copper) of the dose of metallic copper as compared to Kocide® 2000. A similar result is observed in Table 9. COH 20% HB of the present invention exhibits even higher efficacy than commercial copper oxychloride (COC 50%), while using only 16% (120 g/ha vs. 750 g/ha metallic copper) of the dose of metallic copper as compared to commercial COC 50%.

What is claimed is:

1. A fungicide/bactericide composition comprising:

(a) a complex of copper and a carboxylic acid derivative, in which the ratio of copper and carboxylic acid derivative is between 1:0.07 and 1:0.19 based on the weight of copper compound and carboxylic acid derivative;

(c) a first dispersant, wherein said first dispersant is selected from the group consisting of a block copolymer non-ionic surfactant having an average molecular weight of between 1,000 and 15,000, a polyacrylic acid derivative having a pH of between 5 and 10 and an average molecular weight of between 1,000 and 37,000, and combinations thereof; and (e) a second dispersant, wherein said second dispersant is selected from the group consisting of lignin sulfonate, naphthalene sulfonate and combinations thereof, and wherein the weight of said copper compound is between 5% and 39% of the total weight of said composition.

2. The composition of claim 1 wherein said carboxylic acid derivative is citric acid or sodium citrate.

3. The composition of claim 1, wherein said complex comprises citric acid and $Cu^{2+}$, wherein the source of said $Cu^{2+}$ is copper hydroxide.

4. The composition of claim 1, wherein said complex comprises sodium citrate and $Cu^{2+}$, wherein the source of said $Cu^{2+}$ is copper hydroxide.

5. The composition of claim 1, wherein said first dispersant is a block copolymer non-ionic surfactant having an average molecular weight of between 1,000 and 15,000.

6. The composition of claim 1, wherein said first dispersant is a sodium salt of polyacrylic acid.

7. The composition of claim 6, wherein said first dispersant is a sodium salt of polyacrylic acid having a pH of between 9 and 10.8.

8. The composition of claim 1, wherein said first dispersant is a combination of a block copolymer non-ionic surfactant having an average molecular weight of between 1,000 and 15,000 and a sodium salt of polyacrylic acid having a pH of between 9 and 10.8.

9. The composition of claim 1, wherein said second dispersant is naphthalene sulfonate.

10. The composition of claim 9, wherein said second dispersant is a sodium salt of naphthalene sulfonate.

11. The composition of claim 1, further comprising a wetting agent, an antifoam agent and a stabilizer.

12. The composition of claim 11, wherein said wetting agent is a fatty alcohol polyglycol non-ionic surfactant.

13. The composition of claim 11, wherein said antifoam agent is a polydimethylsiloxane antifoam emulsion.

14. The composition of claim 1, comprising the following ingredients: a complex of copper hydroxide and citric acid, a block copolymer non-ionic surfactant having an average molecular weight of between 1,000 and 15,000, a sodium salt of polyacrylic acid having a pH of between 9 and 10.8, diatomaceous earth, calcium carbonate naphthalene sulfonate, a fatty alcohol polyglycol non-ionic surfactant, a polydimethylsiloxane antifoam emulsion and glycerol.

* * * * *